United States Patent [19]

Beregi et al.

[11] 4,259,335

[45] Mar. 31, 1981

[54] 1-METHYL-4-PIPERIDINOL ESTERS OF 4-QUINOLINYLAMINO BENZOATES AND ANTIINFLAMMATORY AND ANALGESIC COMPOSITIONS AND METHODS EMPLOYING THEM

[75] Inventors: Laszlo Beregi, Boulogne Billancourt; Pierre Hugon, Rueil Malmaison; Jacques Buré, Neuilly; Francoise Degrand, Versailles, all of France

[73] Assignee: Science Union et Cie, Societe Française de Recherche Medicale, Suresnes, France

[21] Appl. No.: 64,091

[22] Filed: Aug. 6, 1979

[30] Foreign Application Priority Data

Aug. 1, 1978 [CH] Switzerland ............... 9229/78

[51] Int. Cl.³ ............... A61K 31/47; C07D 401/12
[52] U.S. Cl. ............... 424/258; 546/161
[58] Field of Search ............... 424/258; 546/161

[56] References Cited

U.S. PATENT DOCUMENTS

| | | | |
|---|---|---|---|
| 3,449,347 | 6/1969 | Allais et al. | 546/161 |
| 3,463,780 | 8/1969 | Allais | 546/161 |
| 3,579,520 | 5/1971 | Bailey | 424/258 X |
| 3,910,922 | 10/1975 | Allais et al. | 546/161 |
| 3,944,555 | 3/1976 | Farthouat et al. | 546/161 |
| 3,971,789 | 7/1976 | Archibald et al. | 546/161 |

OTHER PUBLICATIONS

Rovel, et al., Ann. Chim. Rome, 67, No. 9-12, pp. 733-743 (1977).
Moolenaar, et al., International Journal of Pharmaceutics, 4, pp. 195-203 (1980).
Pottier, et al. European J. of Drug Metabolism & Pharmacokinetics, 1979, No. 2, pp. 109-115.
Lynn, et al., J. Clin. Pharmacol., Jan., 1979, pp. 20-30.

*Primary Examiner*—Donald G. Daus
*Assistant Examiner*—Diana G. Rivers
*Attorney, Agent, or Firm*—Omri M. Behr

[57] ABSTRACT

1-methyl-4-piperidinol esters of the formula:

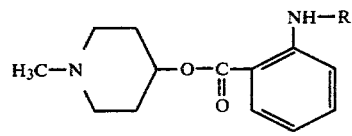

in which R is 7-chloro-4-quinolyl, 7-trifluoromethyl-4-quinolyl or 8-trifluoromethyl-4-quinolyl.

These compounds and physiologically tolerable acid addition salts thereof may be used as medicines especially in the treatment of inflammatory processes and painful syndroms.

12 Claims, No Drawings

1-METHYL-4-PIPERIDINOL ESTERS OF 4-QUINOLINYLAMINO BENZOATES AND ANTIINFLAMMATORY AND ANALGESIC COMPOSITIONS AND METHODS EMPLOYING THEM

The present invention provides 1-methyl-4-piperidinol esters of the formula:

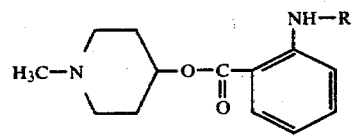

in which R is selected from the group consisting of 7-chloro-4-quinolyl, 7-trifluoromethyl-4-quinolyl and 8-trifluoromethyl-4-quinolyl.

The present invention also provides acid addition salts of the compounds of the formula I. The acid addition salts are preferably physiologically tolerable acid addition salts. As acids which may be used for the formation of these salts there may be mentioned for example hydrochloric, hydrobromic, sulfuric, methanesulfonic and isethionic acids.

The present invention further provides a process for preparing the compounds of the formula I which comprises reacting a chloro compound of the formula:

R—Cl (II)

in which R has the meaning given above, with 1-methyl-4-piperidyl 2-aminobenzoate of the formula:

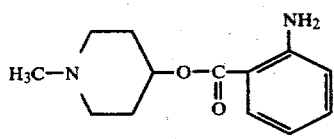

The starting materials of the formula II are described in the literature and prepared either according to H. R. SYNDER and als.'s method, Journal of American Chemical Society 69, 371–374 (1947) when R represents 7-chloro-4-quinolyl or 7-trifluoromethyl-4-quinolyl, or according to the method described in German Offenlegungsschrift No. 1,815,467 and mentioned in Chemical Abstract 71, 9,130v, when R represents 8-trifluoromethyl-4-quinolyl.

1-methyl-4-piperidyl 2-aminobenzoate of the formula II is itself a new product which was prepared by catalytic reduction of the corresponding nitro compound of the formula:

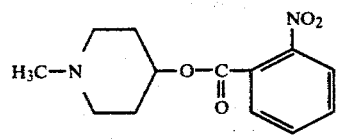

Such a process is advantageously performed by reducing the nitro compound under a hydrogen pressure of about 8 kg/cm² in the presence of Raney nickel as catalyst, the reduction being carried out in an suitable solvent such for example as ethanol at a temperature within the range of from 20° to 80° C.

2-nitrobenzoate of the formula IV was itself prepared according to James A. Waters's method, J. Med. Chem. 21, 628 (1978), starting from 2-nitrobenzoic acid chloride and 1-methyl-4-piperidinol.

The following examples illustrate the invention, the parts being by weight and the melting points being determined on the Kofler hot plate.

EXAMPLE 1

1-methyl-4-piperidyl 2-[(7-trifluoromethyl-4-quinolyl)amino]benzoate.

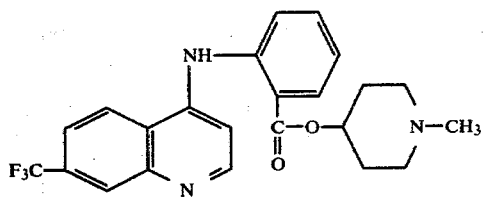

To a solution of 18.7 parts of 1-methyl-4-piperidyl 2-aminobenzoate in 120 parts of a 2 N hydrochloric acid solution, there were added 18.5 parts of 4-chloro-7-trifluoromethyl quinoline, prepared according to SYNDER H. R. and als., J.A.C. S.69, 371–374 (1947). The mixture was refluxed for one hour. After cooling, the precipitate was filtered off, washed with ether and dried.

The raw product (27 parts) is treated with 1500 parts of water and filtered. After alkalinisation with 100 parts of a 2 N solution of sodium hydroxide, the mixture was treated with 500 parts of benzene. The organic layer was dried over magnesium sulfate, then the solvent was evporated off. After recrystallisation from cyclohexane, there were obtained 14,5 parts of 1-methyl-4-piperidyl 2[(7-trifluoromethyl-4-quinolyl)amino]benzoate, melting at 116° C.

EXAMPLES 2-3

The following compounds were prepared according to the process described in Example 1:
(2) 1-methyl-4-piperidyl 2-[(8-trifluoromethyl-4-quinolyl)amino]benzoate, M.P. 181°–182° C., starting from 1-methyl-4-piperidyl 2-aminobenzoate and 4-chloro-8-trifluoromethyl quinoline, itself prepared according to German Offenlegungsschrift No. 1,815,467.
(3) 1-methyl-4-piperidyl 2-[(7-chloro-4-quinolyl)amino] benzoate, M.P. 121°–122° C. (ether), starting from 1-methyl-4-piperidyl 2-aminobenzoate and 4,7-dichloro quinoline, itself prepared according to SYNDER H. R. and als. J.A.C.S. 69, 371–374 (1947)

The compounds of the general formula I and physiologically tolerable salts thereof possess valuable pharmacological and therapeutic properties, especially antiinflammatory and antalgic properties.

Their toxicity is low and their $LD_{50}$ determined in mice per oral route may reach to 1200 mg/kg and, in all cases, is at least 10 times higher than the studied pharmacological activity.

The acute anti-inflammatory activity of the compounds of the present invention was studied in the rats according to the method of WINTER, C. H. and als. Proc. Soc. Exp. Biol. Med. (1962) 111, 554. The compounds of the present invention, when administered in the rats at a dose of 40 mg/kg per os give an inhibition of the plantar edema induced by carrageenin which may reach 34%. Phenylbutazone, a well-known anti-inflammatory agent, gives at the same dose and under the same conditions, an inhibition of 19% of this edema.

The acute antalgic activity of the compounds of the present invention was studied in mice according to the method of HENDERSHOT, L. C. and als., J. Pharm. Ex. THER. (1959), 125, 237. The compounds of the present invention, when administered in mice at a dose of 100 mg/kg per os, give an inhibition of the painful cramps induced by phenylbenzoquinone I.P. which may reach 58.5% one hour after the treatment. This inhibition is maintained at about 36%, 3 hours and even 6 hours after the treatment.

At the same dose and under the same conditions, glafenine, a well-known antalgic agent, give an inhibition of this painful effect of 53%, one hour after the treatment. This inhibition decreases until about 11%, 3 hours after the treatment, and is reduced to zero 6 hours after the treatment. These results show the significant long lasting action of the compounds of the present invention when they are compared with glasfenine.

The chronic activity of the compounds of the present invention was shown by the inhibition test of the granulomatous reaction induced by implanted cotton pellets in the rats according to the method of MAYER, R. K. and als. Proc. Soc. Exp. Biol. Med. (1953) 84,624. There was so observed that the compounds of Example 1, named 1-methyl-4-piperidyl 2-[(7-trifluoromethyl-4-quinolyl)amino] benzoate, is significantly active at a dose of 30 mg/kg per os, while glafenine is very weakly active at 120 mg/kg per os. At a dose of 60 mg/kg per os, the compound of Example 1 shows an activity analogous to the one of phenylbutazone.

This chronic activity was also determined by the inhibition test of arthritis induced by the Freund's adjuvant according to the method of Newbould, B. B., Brit. J. Pharmac. Chemother. (1963) 21, 127. When the products are administered in the rats from the day No. 14 to the day No. 20 at a dose of 40 mg/kg per os, the compound of Example 1 shows a significant activity analogous to the one of phenylbutazone on inflammation and pain, while glafenine has no significant activity at such a dose. When the products are administered in the rats from the day zero to the day No. 13 at a dose of 20 mg/kg per os, the compound of Example 1 is active when the treatment is stopped and seven days later on inflammation, pain and seromucoids, while glafenine gives only an effect on pain and an unlasting decrease of seromucoids.

On the other hand, the histological examination of kidneys of rats treated for two days with the compound of Example 1 shows that at doses of 150 and 300 mg/kg per os, this compound gives no renal change. On the contrary, at the same doses and under the same conditions, glafenine gives at different degrees some areas of very dilated nephrons which may go until patent histological signs of tubulopathy.

The above pharmacological properties and the low toxicity of the compounds of the general formula I and physiologically tolerable salts thereof enable their use in therapy especially in the treatment of acute and chronic inflammation and its attendant pain. So they may be used especially in the treatment of rheumatic diseases (polyarthritis, spondylitis etc.) in inflammatory pathology in conjunction with degenerative or traumatic process (lombosciatica, painful shoulder, postoperative inflammation etc.). Moreover, this anti-inflammatory effect finds its application in the fields where classical medications produce some side or toxic effects, especially in renal pathology (treatment of glomerulitis and nephritis) and in ulcerous pathology.

The present invention also provides pharmaceutical compositions containing as active ingredient a compound of the formula I or a physiologically tolerable salt thereof, in admixture or conjunction with a pharmaceutically suitable carrier such for example as distilled water, glucose, lactose, starch, talc, ethylcellulose, magnesium stearate or cocoa butter.

The so-obtained pharmaceutical compositions are advantageously in unit dosage forms and may contain from to 50 to 500 mg of active ingredient. They may be for example in form of tablets, dragees, capsules, suppositories injectable solutions or ointments and be administered by oral, rectal, parenteral or topical route at doses within the range of from 50 to 500 mg once to four times a day.

We claim:

1. A compound selected from the group consisting of: 1-methyl-4-piperidinol esters of the formula:

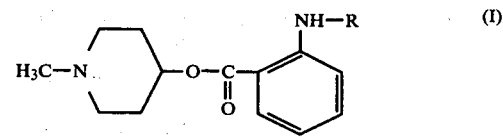

in which R is selected from the group consisting of
7-chloro-4-quinolyl, 7-trifluoromethyl-4-quinolyl and
8-trifluoromethyl-4-quinolyl; and
physiologically tolerable salts thereof.

2. A compound of claim 1 which is 1-methyl-4-piperidyl 2-[(7-trifluoromethyl-4-quinolyl)amino] benzoate.

3. A compound of claim 1 which is 1-methyl-4-piperidyl 2-[(8-trifluoromethyl-4-quinolyl)amino] benzoate.

4. A compound of claim 1 which is 1-methyl-4-piperidyl 2-[(7-chloro-4-quinolyl)amino] benzoate.

5. An anti-inflammatory composition comprising an anti-inflammatorily effective amount of a compound of claim 1 and a pharmaceutically acceptable carrier.

6. A composition of claim 5 comprising from 50 to 500 milligrams of the anti-inflammatorily effective compound per unit dosage.

7. An analgesic composition comprising an analgetically effective amount of a compound of claim 1 and a pharmaceutically acceptable carrier.

8. A composition of claim 7 comprising from 50 to 500 milligrams of the analgetically effective compound per unit dosage.

9. A method of reducing inflamation in a living body affected by acute or chronic inflammation which comprises administering an anti-inflammatory effective amount of a compound of claim 1 to said body.

10. A method of claim 9 which comprises administering between 50 and 500 milligrams of the anti-inflammatorily effective compound from one to four times per day.

11. A method of reducing pain in a living body affected by acute or chronic inflammation which comprises administering an analgetically effective amount of a compound of claim 1 to said body.

12. A method of claim 11 which comprises administering between 50 and 500 milligrams of the analgetically effective compound from one to four times per day.

* * * * *